United States Patent [19]

Cooper et al.

[11] 4,038,864
[45] Aug. 2, 1977

[54] HYDROCARBON MEASUREMENT

[75] Inventors: John C. Cooper, Eugene; Harvey E. Birdseye, Cottage Grove; Russell J. Donnelly, Eugene, all of Oreg.

[73] Assignee: State Board of Higher Education for and on Behalf of the University of Oregon, Eugene, Oreg.

[21] Appl. No.: 514,448

[22] Filed: Oct. 15, 1974

[51] Int. Cl.$^2$ ............................................ G01N 31/00
[52] U.S. Cl. .................................................... 73/23
[58] Field of Search ........................ 73/23, 19, 25, 29; 23/232 R, 254 R, 254 EF

[56] References Cited

U.S. PATENT DOCUMENTS

| | | | |
|---|---|---|---|
| 2,286,384 | 6/1942 | Sanderson | 73/23 |
| 2,327,060 | 8/1943 | Pollak et al. | 73/23 |
| 2,420,648 | 5/1947 | Bolton | 73/29 |
| 3,027,241 | 3/1962 | Andreatch et al. | 23/254 EF |
| 3,194,054 | 7/1965 | Deaton et al. | 73/25 |
| 3,236,603 | 2/1966 | Durrett et al. | 23/254 R |
| 3,607,096 | 9/1971 | Hartmann | 23/254 EF |
| 3,662,588 | 5/1972 | Emerson et al. | 73/23 |

Primary Examiner—Richard C. Queisser
Assistant Examiner—Stephen A. Kreitman
Attorney, Agent, or Firm—Kolisch, Hartwell, Dickinson & Stuart

[57] ABSTRACT

Apparatus and method relating to the monitoring of a gas supply to determine the level of certain gas constituents in the supply. There is disclosed a method of monitoring air to determine the hydrocarbon content thereof exclusive of methane. Air is fed through a cold trap maintained at a temperature which produces condensation of the higher hydrocarbons normally found in ambient air at an urban location. Methane, however, passes through the trap. From the cold trap the air is directed to an analyzer, which continuously analyzes the air for hydrocarbon content. Air having all original hydrocarbons is fed the analyzer during intervals interspersed with intervals when the air fed the analyzer has had higher hydrocarbons removed. By comparing the hydrocarbon content of the two types of air, one is enabled to determine the content in such air of hydrocarbons exclusive of methane.

5 Claims, 3 Drawing Figures

HYDROCARBON MEASUREMENT

The Government has rights in this invention pursuant to Grant GI-42546 awarded by the National Science Foundation.

This invention relates generally to apparatus and method for monitoring a gas supply, to determine the level of certain gas constituents in the supply. More particularly, the invention concerns a method of monitoring impure air, to determine the hydrocarbon content thereof, and apparatus for performing this and similar types of analyses.

Many of the hydrocarbon contaminants in impure air take part in the photochemical reactions that form smog, but methane, which occurs naturally at relatively high levels, apparently is not a significant factor in this type of reaction. Studies have shown that typically methane is present at levels above 1 ppm, and constitutes perhaps half of the total hydrocarbon level in an urban atmosphere. The ratio of methane to nonmethane hydrocarbons varies so widely, however, that total hydrocarbon measurements may not be relied upon to obtain an accurate determination of hydrocarbons other than methane, i.e., the smog generation potential. Accordingly, ambient air standards for hydrocarbons as set forth by environmental agencies typically make reference to nonmethane-tyope hydrocarbons.

Systems have been proposed for separately measuring methane and total hydrocarbons in ambient air. The methane measurement is performed by gas chromatography, and using a flame ionization detector. However, gas chromatography is inherently a batch process, and as performed at present requires several minutes per an analysis. As a consequence, the approach cannot follow the rapid hydrocarbon fluctuations occurring in the normal urban atmosphere.

One object of this invention is to provide a novel method for monitoring ambient air, and determining the hydrocarbon content thereof, which analyzes on a substantially continuous basis, as compared to the batch-type processing of methods relying upon gas chromatography.

Another object of the invention is to provide novel apparatus for monitoring gases from a gas supply, featuring a flame ionization detector, and means for introducing to the detector a continuous flow of gas to be subjected to analysis, a portion of such flow being processed by a cryogenic or cold trap for the purpose of removing condensables, and another portion of such flow bypassing the trap.

Yet another object of the invention is to provide novel apparatus for monitoring ambient air, which includes a cold trap for removing from such air condensables such as the higher hydrocarbons, and means for operating the cold trap at a subatmospheric pressure condition, to inhibit the condensation of a gas such as oxygen.

These and other objects and advantages will become more fully apparent from the following description to be read in conjunction with the accompanying drawings, wherein.

Figure 1:
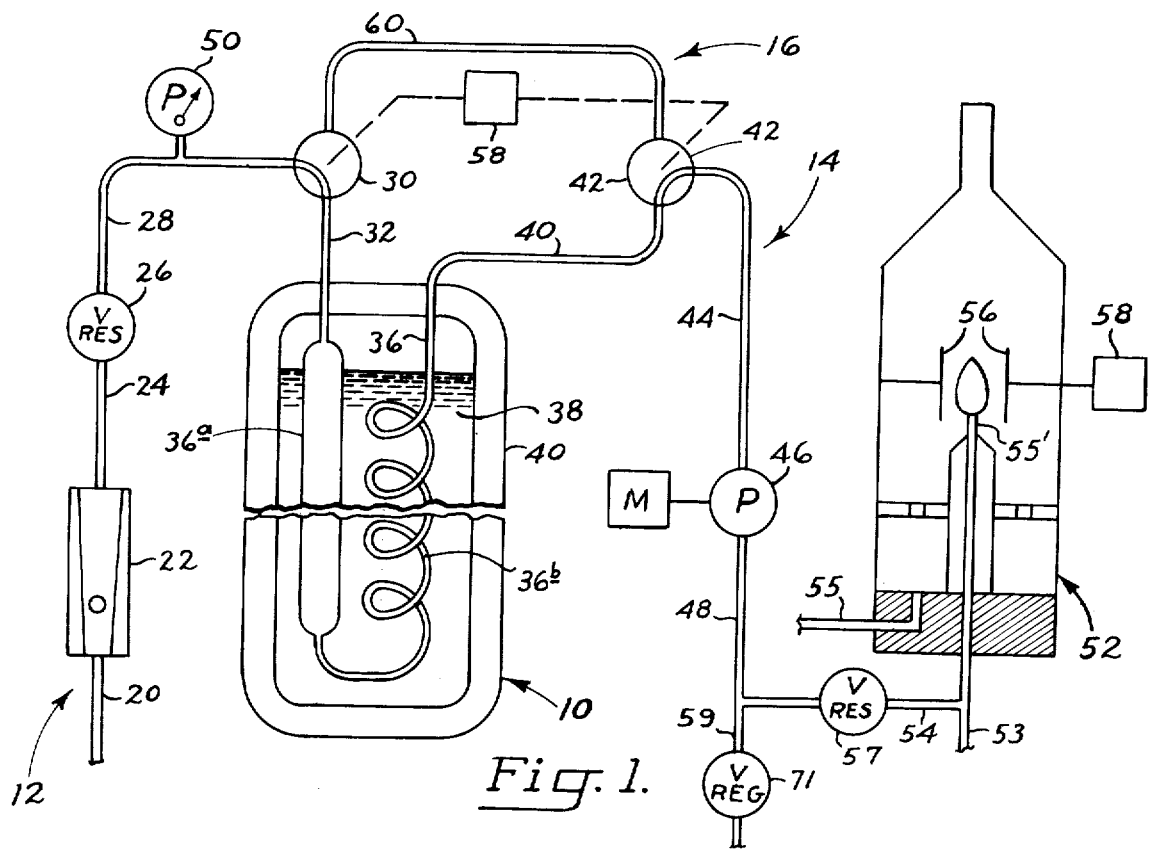
FIG. 1 illustrates schematically apparatus as comtemplated herein.

Referring to FIG. 1, the apparatus illustrated comprises a cryogenic or cold trap 10, which is fed gas from a supply, i.e., the atmosphere in the case of equipment for monitoring ambient air, through a conduit means indicated generally at 12. Gas leaving the trap is fed to an analyzer through a conduit means indicated at 14. Another conduit means is shown at 16 which provides a bypass for trap 10, and is operable to connect the atmosphere with the analyzer with bypassing of the trap.

Considering in further detail conduit means 12, such includes an inlet line or pipe 20 communicating with the atmosphere meter with a needle valve 26, referred to herein also as a restricting valve, or means, which functions to restrict the flow of gas downstream from the needle valve. Line 28 connects the needle valve with the inlet side of a timer controlled valve 30. Connecting one of the exhaust ports of this valve with what is referred to herein as the inlet end of the cryogenic trap is a line 32.

The cryogenic trap comprises a U-tube 36 submersed in a pool of coolant, shown at 38. In monitoring ambient air, liquid nitrogen which boils at approximately 77° K. may be employed as the coolant. Confining the coolant is a Dewar 40.

U-tube 36 includes an inlet section shown at 36a, and a coiled tubular section shown at 36b. In a specific embodiment of the invention, the inlet section consisted of a 6 inch long ¼ inch diameter stainless steel tube, and the coiled tubular section consisted of ⅛ inch diameter copper refrigeration tubing 160 inches in length. Ambient air from the atmosphere ordinarily includes a certain amount of water vapor and minor amounts of carbon dioxide. In operating the trap, these tend to condense first and collect as solid deposits within the U-tube. By providing the inlet section described, having the somewhat larger diameter than the remainder of the U-tube, the trap may be operated without early clogging by reason of the formation of such deposits.

Considering now in more detail conduit means 14, the discharge end of the cold trap is connected by line 40 to one of the ports of a second timer controlled valve 42. Another port of the valve is connected by line 44 to the suction side of a vacuum pump 46. Connecting the discharge side of pump 46 to an analyzer is a line 48.

At 77° K., or the temperature at which the cold trap is operated, there is a tendency for air to condense, with such eventually filling the trap with liquid. This tendency may be inhibited by operating the trap at a subatmospheric pressure. Thus, under normal conditions, the apparatus illustrated has been operated, when monitoring ambient air for hydrocarbon content, at pressures (absolute) below about 24 inches of mercury. Pump 46 and needle valve 26 provide a means for maintaining such a pressure condition within the trap with the pump operating to pull air through the trap against the restricting action provided by the needle valve. A gauge 50 connected to line 28 indicates the pressure within this line.

The analyzer in the embodiment of the invention shown in Fig. 1 is a hydrogen flame ionization detector 52. Such an analyzer, as is well known in the art, is effective continuously to analyze a continuous stream of gas fed thereto. The detector includes a hydrogen gas inlet 53, and the gas which is to be analyzed in the analyzer is introduced into inlet 53 by line 54 including restricting valve 57 connecting with line 48 earlier described. Also connecting with line 48 is a line 59 provided with a constant pressure regulating valve 71 venting to the atmosphere. The valve is adjusted whereby the pressure of the air being analyzed and supplied from pump 46 is at some predetermined level (normally in the range of three to five pounds per square inch gauge), excess air supplied the pump being exhausted into the atmosphere through the regulating valve. A burner 55' within the detector produces a hydrogen flame. A burner air inlet is shown at 55.

Electrodes 56 measure the ionization current across the flame, and this measurement or signal is transmitted by suitable circuitry to the output 58 of the device. The output of the device is normally graphically recorded as on a chart of the type illustrated in FIG. 2.

Valves 30, 42 are controlled by a timer shown at 58. With the valves in the positions shown, line 28 is in communication with line 32, and line 40 commumicates with line 44, with the result that flow of air through the device from the atmosphere will be through the first conduit means 12, the cryogenic trap, and conduit means 14, into ionization detector 52. Timer 58 is operable periodically to adjust valves 30, 42 whereby line 28 communicates with a line 60 through valve 30 and line 60 communicates with line 44 through valve 42. With this adjustment of the parts, line 60, which constitutes a third or a bypass conduit means, provides a passage for the flow of air to the ionization detector with such air not subjected to any hydrocarbon removal by the trap.

Figure 2:
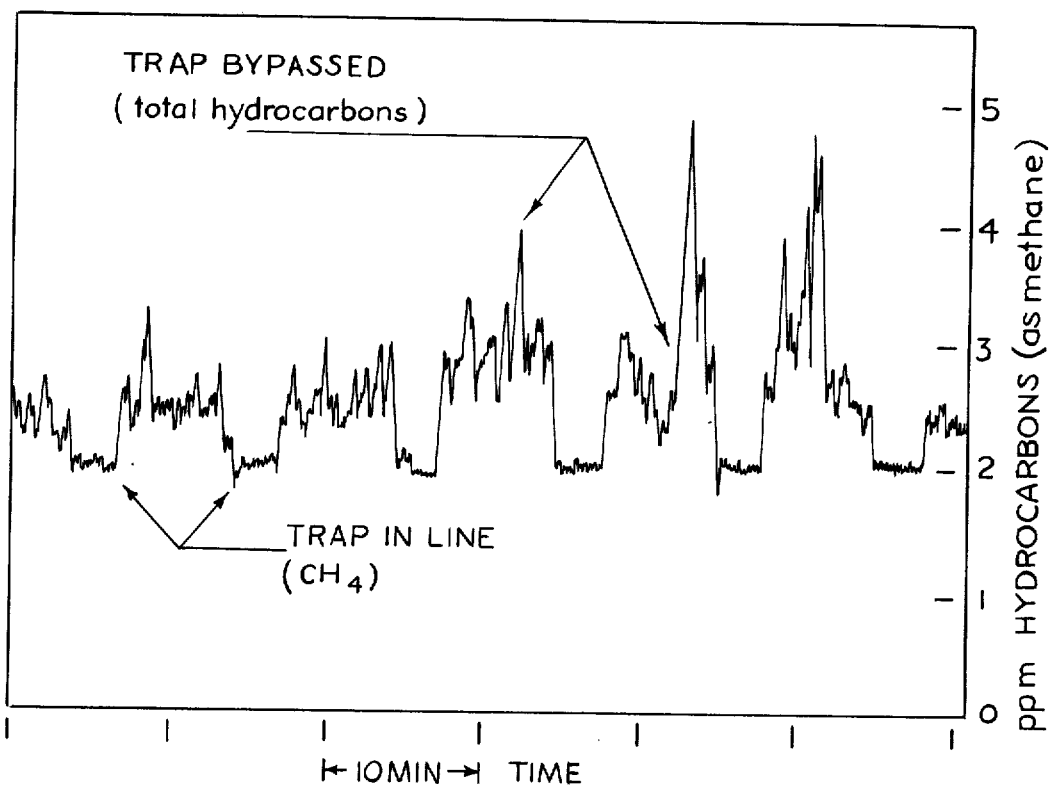
FIG. 2 is exemplary of a chart obtained from a hydrogen flame ionization detector utilizing apparatus of the type illustrated in FIG. 1.

In operating the apparatus described, air is continuously fed into the ionization detector by pump 46. Periodically, and for a selected time interval, the air fed into the detector is the air which passes through the trap, with such trap being effective to remove from the air hydrocarbons other than methane. Over time intervals interspersed with the time intervals during which there is hydrocarbon removal, air fed into the detector travels though the bypass conduit means, and, as a consequence, such air has all original hydrocarbons therein. Over both sets of time intervals, the detector effects a continuous reading of the hydrocarbon content of such air (from which hydrocarbons expressed as methane may be determined), and such is recorded graphically as illustrated in FIG. 2.

A device of the type described was used in monitoring the hydrocarbon content of ambient air in a municipality of approximately 100,000 population. The timer mechanism was adjusted whereby the air supplied the ionization detector was directed through the trap for three minute periods, alternating with intervals or periods of seven minutes when the air bypassed the trap and traveled through line 60. The output of the ionization detector graphically portrayed is set forth in FIG. 2. It will be noted that for the three minute periods during which the air traveled through the trap, relatively stable lower levels of hydrocarbon are indicated, with the air containing approximately 2 ppm hydrocarbon expressed as methane. During the seven minute intervals, when the bypass was used, it will be noted that the trace line on the graph is more variable with the indicated level of hydrocarbon content varying from about 2.5 to as high as 5 ppm. Operated in this manner, the apparatus establishes a base line corresponding to the relatively stable methane levels, with the nonmethane hydrocarbon levels being measured above this base line.

Figure 3:
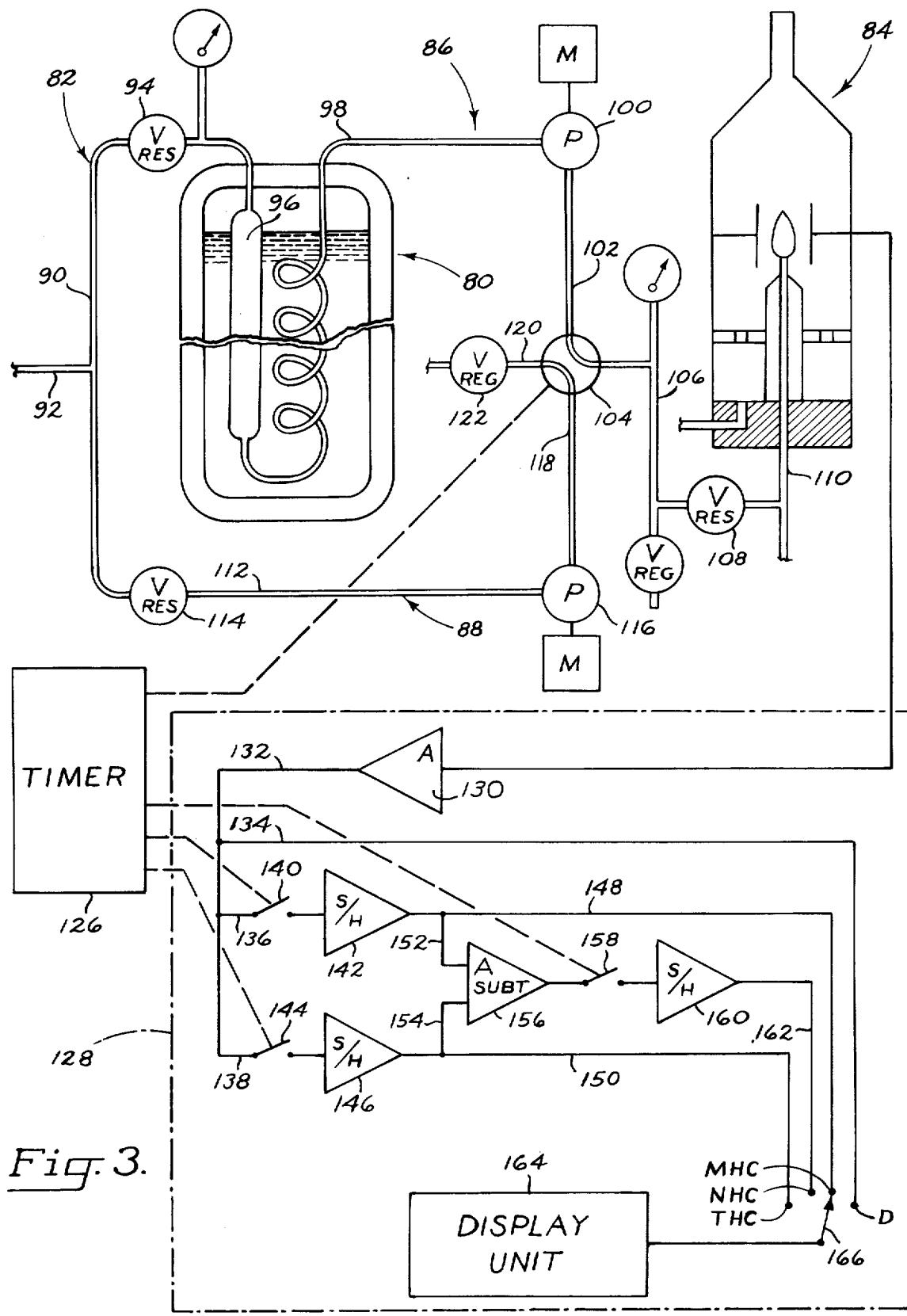
FIG. 3 illustrates schematically a modified form of apparatus.

A modified form of apparatus as contemplated by the invention is illustrated in FIG. 3. Referring to this figure, a cold trap is shown at 80. Gas from a supply, i.e., the atmosphere, is introduced to the cold trap through conduit means 82. Gas leaving the cold trap is fed to an analyzer 84 through a conduit means 86. A bypass for the cold trap is provided in the form of a conduit means 88.

Conduit means 82 includes a line 90 communicating to the atmosphere through line 92. Line 90 is provided with a restricting valve 94 and connects with the inlet end of the trap 80, more specifically the inlet end of U-tube 96.

Considering conduit means 86, it comprises a line 98 connected to the discharge end of the cold trap and feeding the suction side of a vacuum pump 100. The discharge side of the pump is connected by a line 102 to a timer-controlled valve 104. Also connected to the valve 104 is a line 106 provided with a restricting valve 108 connecting with hydrogen inlet 110 supplying analyzer 84. With valve 104 having the adjusted position shown in FIG. 3, the air supplied the analyzer is air which has passed through the cold trap to have all hydrocarbons but methane removed therefrom.

Considering bypass conduit means 88, such includes a line 112 provided with a restricting valve 114 connecting with line 92 which communicates with the atmosphere. Line 112 also connects with the suction side of a pump 116. Connecting with the discharge side of pump 116 is a line 118 which also connects with valve 104. Shown at 120 is another line connected with valve 104, which vents to the atmosphere and is provided with a constant pressure regulating valve 122.

Valve 104 is adjustable from the position shown in FIG. 3 to a position connecting line 102 with line 120, wherein air discharged by pump 100 is directed into the atmosphere through regulating valve 122. In this other position of adjustment, air flowing in line 118 is delivered through valve 104 to line 106, thence to be fed into hydrogen inlet 110.

With the apparatus illustrated in FIG. 3, the volume capacity of line 90, U-tube 96, line 86 and line 102, i.e., the conduit system supplying air from the atmosphere to the location of valve 104, is selected to be substantially greater than the capacity of lines 112, 118, i.e., the conduit system supplying air from the atmosphere to valve 104 with such air bypassing the cold trap. Because of the larger capacity of the first described conduit system, and with vacuum pumps 100, 116 pumping air at substantially the same rate through the two systems, the apparatus permits the continuous analysis of streams of air in analyzer 84 with one stream of air containing all original hydrocarbons and the other stream containing only methane, but with the two streams of air having been taken from the atmosphere at the same point in time.

Further explaining, let it be assumed that the capacity of the system which includes the cold trap is sufficiently greater than the capacity of the system bypassing the cold trap that it takes approximately 30 seconds longer for air to travel through the first described system than the second, i.e., there is a 30 second delay in the travel time through the first described system. This being the case, it is possible with the apparatus described to analyze the air flowing through the bypassing system for a 30-second time interval, with value 104 adjusted so that line 118 supplies line 106, and after such 30-second period and with valve 104 adjusted so that line 102 supplies line 106, to analyze air passing through the cold trap, such air having been removed from the atmosphere at the same point in time as the air previously analyzed and supplied by line 118. The air delivered through the cold trap is air with all hydrocarbons but methane removed, as opposed to the air first analyzed which contained all original hydrocarbons. The nonmethane hydrocarbon level may then be determined with reference to a continuously flowing air sample taken at the same point in time from the atmosphere, by comparing the hydrocarbon levels noted in the two streams of air.

With continuing reference to FIG. 3, timer-controlled valve 104 is controlled by timer 126. Timer 126 also controls output 128 receiving the measurement or signal transmitted to the output from the ionization detector 84.

Discussing in more detail the electronic circuitry involved in output 128, the signal from detector 84 passes through an amplifier 130 to a conductor 132. From conductor 132 the signal is supplied to three conductors indicated at 134, 136 and 138.

A signal supplied conductor 136, and with timer controlled switch 140 closed, is fed to a sample and hold amplifier shown at 142. As is conventional with such amplifiers, such functions to produce an output signal which is an amplification of the signal fed thereinto, and with opening of the circuit feeding the amplifier the output signal produced at the moment of such opening is held or sustained. With subsequent closing of the circuit feeding the amplifier, it is the new signal then received which is amplified. A signal supplied conductor 138, and with timer-controlled switch 144 closed, is fed to a similar sample and hold amplifier 146.

The output of amplifier 142 is supplied a conductor 148, and similarly the output of amplifier 146 is supplied a conductor 150. Conductor 152 connecting with conductor 148, and conductor 154 connecting with conductor 150, supplies signals fed to conductors 148, 150 to a subtracting amplifier 156. Such subtracting amplifier is conventional, in that it subtracts the two signals supplied the amplifier and amplifies the subtracted result. The output of subtracting amplifier 156, with closing of timer-controlled switch 158, is fed to another sample and hold amplifier indicated at 160, and the output signal of this amplifier is supplied a conductor 162.

Switches 140, 144 and 158 are controlled by timer 126 controlling the operation of valve 104. The timing of switch 140 is such that it closes shortly after the time that valve 104 is adjusted to feed air into analyzer 84 from line 102, and opens shortly before valve 104 is adjusted to feed air into analyzer 84 from line 118, the air analyzed during this period having had all hydrocarbons but methane removed therefrom. As a consequence, the signal which is supplied to display unit 164 by conductor 148, and which is displayed when selector arm 166 of unit 164 is manually adjusted to engage the contact identified as MHC in FIG. 3, is an amplified signal indicative of the methane hydrocarbon content of the air. Assuming that valve 104 is adjusted to a new position every 30 seconds, and the delay in air travel time through the system including the cold trap is as discussed above, switch 104 typically might be closed some 5 seconds after the first adjustment of valve 104 mentioned, and opened some five seconds before the next adjustment.

Switch 144 is timed by the timer to close shortly after valve 104 is adjusted to supply the analyzer with air from line 118, and shortly before valve 104 is adjusted to feed air into the analyzer from line 102, the air analyzed during this period having bypassed the cold trap and as a consequence containing all the hydrocarbons in the ambient air being tested. As a result, display unit 164, with its arm 166 engaging contact THC in FIG. 3, is fed a signal through conductor 150 indicative of the total hydrocarbon content of the air analyzed, such signal having a higher level.

Switch 158 is timed by the timer to be closed for a short time interval (for instance, 2 seconds) after switch 140 has opened and before switch 144 closes. Subtracting amplifier 156 during this time interval feeds a signal to amplifier 160 which is the difference between the sustained outputs of amplifiers 146 and 142, and which is indicative, therefore, of the nonmethane hydrocarbon content of the air. This signal is displayed by the display unit with selector arm 166 engaging the contact labeled NMHC in FIG. 3, and is indicative of the nonmethane hydrocarbons in the ambient air, in samples of such air taken at the same point in time.

With selector arm 166 adjusted to engage contact D in FIG. 3, the signal supplied the display unit 164 is a continuing amplified signal of the type that may be utilized, for instance, in preparing the chart illustrated in FIG. 2.

It will be seen from the above that an apparatus and method is contemplated for monitoring a gas supply such as ambient air, which can rapidly and accurately give an indication of the level of certain constituents in the gas supply. In the measurement of ambient air the method is usable to produce an indication of the level of nonmethane hydrocarbons by comparing the total hydrocarbon level in the air being monitored with the level of methane in such air.

It is claimed and desired to secure by Letters Patent:

1. In apparatus for monitoring a gas supply to determine the level of certain gas constituents in the gas supply, the combination of
   a flame ionization detector, and
   means for introducing gas from said gas supply into said detector,
   said means including a cold trap having feed and discharge ends,
   conduit means connecting said supply to the feed end of said cold trap for feeding gas from the supply to the cold trap, said conduit means including restricting means offering restriction to the flow of gas into the trap,
   another conduit means connecting the discharge end of the cold trap to the ionization detector, said other conduit means including pump means connected so as to pull gas from said supply through said restricting means and said trap,
   a third conduit means connecting said supply to said ionization detector with bypassing of said cold trap, and
   valve means adjustable to produce flow from said supply into said detector selectively either through said cold trap or through said thrid conduit means.

2. The apparatus of claim 1, wherein said third conduit means connects with said supply through joinder with said first conduit means at a point intermediate said restricting means and said cold trap, and said third conduit means connects with said detector through joinder with said other conduit means at a point intermediate said cold trap and said pump means.

3. The apparatus of claim 1, which further includes an automatic timer controlling said valve means.

4. The apparatus of claim 1, wherein said cold trap comprises an elongate tube, and includes adjacent the feed end of the trap an ice collecting section having a bore diameter which is larger than the diameter of remainder portions of the trap located toward said pump means from the ice collecting section.

5. The apparatus of claim 1, wherein said flame ionization detector produces an electrical signal related to the level of certain gas constituents in said supply, and the flame ionization detector is connected to an output device which compares a signal produced by the detector when gas introduced to the detector flows through said cold trap with a signal produced by the detector when the gas introduced the detector flows through said third conduit means.

* * * * *